United States Patent [19]

Albright

[11] 4,003,862
[45] Jan. 18, 1977

[54] N-SUBSTITUTED TETRAHALOPHTHALIMIDES AS FLAME RETARDANTS

[75] Inventor: James A. Albright, Ann Arbor, Mich.

[73] Assignee: Michigan Chemical Corporation, Chicago, Ill.

[22] Filed: Oct. 23, 1975

[21] Appl. No.: 625,052

[52] U.S. Cl. .................. 260/2.5 AJ; 260/2.5 FP; 260/45.8 NE; 260/77.5 SS; 260/326 E; 260/880 R

[51] Int. Cl.² .............. C07D 209/48; C08K 5/34; C08K 5/52

[58] Field of Search .......... 260/45.8 NE, 45.8 NB, 260/326 E, 2.5 AJ, 2.5 FP, DIG. 24, 880 R; 106/15 FP; 252/8.1; 428/921

[56] References Cited

UNITED STATES PATENTS

| | | | |
|---|---|---|---|
| 3,624,024 | 11/1971 | Caldwell et al. | 260/40 |
| 3,663,495 | 5/1972 | Michael et al. | 260/37 |
| 3,803,038 | 4/1974 | Olszewski | 252/49.9 |
| 3,890,275 | 6/1975 | Golborn et al. | 260/45.8 |
| 3,920,685 | 11/1975 | Porret et al. | 260/309.5 |
| 3,925,406 | 12/1975 | Porret et al. | 260/309.5 |
| 3,935,162 | 1/1976 | Golborn et al. | 260/45.9 |
| 3,950,307 | 4/1976 | Richter et al. | 260/45.75 |

FOREIGN PATENTS OR APPLICATIONS 475,539   2/1972   Japan

Primary Examiner—Donald E. Czaja
Assistant Examiner—R. A. White
Attorney, Agent, or Firm—Robert M. Phipps

[57] ABSTRACT

Disclosed are novel compounds of the formula

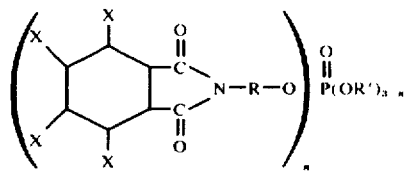

wherein each X is independently selected from chlorine or bromine, R is alkylene having from 1 to 6 carbon atoms, each R' is independently selected from an alkyl or haloalkyl group having from 2 to 6 carbon atoms, and n is 1 to 3. The above compounds are effective flame retardants in flammable polymeric compositions.

11 Claims, No Drawings

N-SUBSTITUTED TETRAHALOPHTHALIMIDES AS FLAME RETARDANTS

BACKGROUND OF THE INVENTION

1. Field of the Invention

Compounds within the field of this invention are cyclic imides of orthodicarboxylic acids.

2. Description of the Prior Art

The use of bis-imides as flame retardants for polymers of olefinically unsaturated aromatic monomers, for example polystyrene and styrene copolymers, as well as the use of tetrahalophthalimides and alkyltetrahalophthalimides as flame retardants are disclosed in the prior art. British Pat. No. 1,287,934 generically discloses bis-imides of the formula

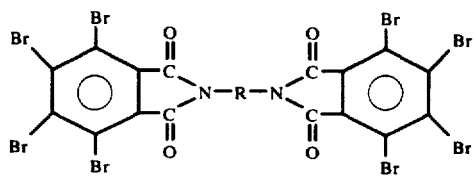

wherein R represents a divalent aliphatic, aromatic, or araliphatic radical which may be substituted by one or more halogen atoms. The use of the above defined bis-imides as flame retardants for, among other things, polystyrene and styrene copolymers, is noted in Br. 1,287,934.

D. S. Pratt et al., "Phthalic Acid Derivatives: Constitution and Color, Some Derivatives of Tetrabromophthalimide", Journal of the American Chemists Society, 40, 1415–1425 (1918) and S. M. Spatz, et al., "Some N-Substituted Tetrabromophthalimide Fire Retardant Additives", Industrial and Engineering Chemistry; Product Research Development, Vol. 8, No. 4, 397–398 (1969), both specifically disclose tetrabromophthalimide. Spatz et al. additionally disclose several specific alkyltetrabromophthalimides.

U.S. Pat. No. 3,623,495, U.S. Pat. No. 3,313,763, and U.S. Pat. No. 3,240,792 each disclose a different tetrahalophthalimide.

However, haloalkylphosphate tetrahalophahalimides have not been disclosed in the art.

During the past several years, a large number of flame retardants have been developed for use with an almost equally large number of flammable materials. Cellulosic materials such as paper and wood and polymeric materials such as synthetic fibers and bulkier plastic articles are just two examples of materials for which flame retardants have been developed. For any class of flammable materials, such as synthetic high polymers, those skilled in the art have long been aware that some flame retardant additives are more effective in some polymers than they are in others. In fact, many flame retardant additives which are highly effective in some polymer systems are virtually ineffective in other polymer systems. The mere fact, therefore, that most flame retardants contain halogen and phosphorus atoms does not assure that any given halogenated or phosphorus-containing compound will impart useful flame retardant characteristics to all or even to any polymeric systems. Furthermore, as those skilled in the art have improved the flame retardancy of many polymeric materials, they have been simultaneously required to provide the necessary flame retardancy with a minimal effect upon other properties of the polymers such as their light stability, moldability and flexural, tensile and impact strengths. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

SUMMARY OF THE INVENTION

Flame retardant compounds of the formula

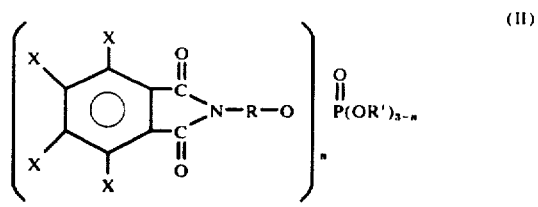

wherein each X is independently selected from chlorine or bromine, R is an alkylene group containing from one to six carbon atoms, each R' is independently selected from an alkyl or haloalkyl group containing from two to six carbon atoms, and wherein the haloalkyl group contains from one to three halogen atoms independently selected from the group comprising chlorine and bromine, and wherein n is one to three.

DESCRIPTION OF THE PREFERRED EMBODIMENTS

The flame retardant compounds within the scope of this invention have the formula II above wherein each X is independently selected from chlorine or bromine, wherein R is an alkylene group containing from one to six carbon atoms, preferably from one to three carbon atoms, wherein each R' is independently selected from an alkyl or haloalkyl group containing from two to six carbon atoms, preferably from two to three carbon atoms, wherein the haloalkyl group contains from one to three halogen atoms, perferably from one to two halogen atoms, independently selected from the group comprising chlorine and bromine, and wherein all R' groups are preferably identical; and wherein n is one to three. For purposes of illustration only, Table I as follows is designed to further help describe the compounds of formula II of this invention and is neither meant nor should it be taken to be a complete listing of all the compounds within the scope of formula II of this invention.

TABLE I

| Compound | X | X | X | X | R | R' | n |
|---|---|---|---|---|---|---|---|
| 1 | Br | Br | Br | Br | —(CH₂)₂— | chloroethyl chloroethyl | 1 |
| 2 | Br | Br | Cl | Cl | —CH₂— | chloroethyl | 2 |
| 3 | Br | Br | Br | Br | —(CH₂)₃— | — | 3 |
| 4 | Cl | Cl | Cl | Cl | —(CH₂)₃— | Bromopropyl | 2 |
| 5 | Br | Br | Br | Br | —CH₂— | 2,3-dichloropropyl 2,3-dibromopropyl | 1 |
| 6 | Br | Br | Br | Br | —(CH₂)₂— | tribromoneopentyl* tribromoneopentyl | 1 |
| 7 | Br | Br | Br | Br | —(CH₂)ₙ— | ethyl | 2 |
| 8 | Cl | Cl | Cl | Cl | —(CH₂)₄— | — | 3 |
| 9 | Br | Br | Br | Br | —(CH₂)₂— | — | 3 |
| 10 | Br | Br | Br | Br | —(CH₂)₂— | 2,3-dibromopropyl | 2 |
| 11 | Br | Br | Br | Br | —(CH₂)₃— | 2,3-dibromopropyl 2,3-dibromopropyl | 1 |

TABLE I-continued

| Compound | X | X | X | X | R | R' | n |
|---|---|---|---|---|---|---|---|
| 12 | Cl | Cl | Cl | Cl | —(CH₂)₃— | 2,3-dichloropropyl 2,3-dichloropropyl | 1 |

*tribromoneopentyl has the graphic formula of

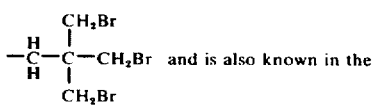

literature as 2,2-bis-(bromomethyl)-3-bromopropyl.

The compounds within the scope of this invention can be prepared by heating an equimolar mixture of the tetrahalophthalic anhydride and an alkanol amine to such temperature as is necessary to drive off the water, e.g., from about 50° to 150° C. This can be done in a variety of solvent systems, e.g., xylene, dimethylformanide, glycols, isopropanol, etc. by techniques well known to those skilled in the art. This procedure yields immediate hydroxyalkyltetrahalophthalimides. A further discussion on the synthesis of hydroxyalkyltetrahalophthalimides may be found in Spatz et al.

The intermediate hydroxyalkyltetrahalophthalimide is further reacted with substituted or unsubstituted phosphoryl chlorides in the presence of metal catalysts known to those skilled in the art, e.g., magnesium oxide, titanium tetrachloride, magnesium chloride, stannous chloride, etc. to obtain the N-substituted tetrahalophthalimides of formula II of this invention. Said reaction between the intermediate hydroxyalkyltetrahalophthalimide and the phosphoryl chloride is conducted using a molar ratio of said reactants consistent with the desired flame retardant II final product. This reaction can also be carried out in the presence of a tertiary amine catalyst such as pyridine, triethylamine, etc. The reaction can also be carried out with or without an inert solvent such as an aromatic, e.g., xylene, benzene or toluene, haloalkanes, e.g., perchloroethylene, or chloroform, ethers and the like. The reaction is carried out until the theoretical amount of hydrogen chloride has been eliminated. This reaction generally takes place at from 0° to 120° C. depending upon the choice of solvent and/or catalyst employed.

The final product may optionally be further purified by standard procedures well known to those skilled in the art, for example, recrystallization or washing with common organic solvents, e.g., benzene, acetone, methanol, etc., and water.

The flame retardants within the scope of this invention can be used in combination with virtually any flammable elastomeric or polymeric material. The material may be macromolecular, for example, a cellulosic material or a polymer. Among polymers with which the flame retardants of this invention may be combined may be mentioned, for example, olefin polymers, for example, homopolymers of ethylene, propylene or butene, copolymers of two or more monomers and copolymers of one or more such monomers with other copolymerizable monomers, for example ethlene/propylene copolymers, ethylene/ethylacrylate copolymers and ethylene/vinyl acetate copolymers; polymers of olefinically unsaturated aromatic monomers, for example, polystyrene and styrene copolymers; polyurethanes; polyamides; polyimides; polyesters, epoxy resins; phenolic polymers; elastomers; for example, butadiene/styrene copolymers, butadiene/acrylonitrile copolymers and terpolymers of acrylonitrile, butadiene, and styrene; natural rubber; butyl rubber; and polysiloxanes. The flame retardants of formula II within the scope of this invention are especially useful in polyurethanes, both rigid and flexible as well as elastomers; polystyrenes, both foamed and high-impact; acrylonitrile/butadiene/styrene terpolymers; epoxy resins; and unsaturated polyesters.

The flame retardants of this invention may be incorporated into or applied onto virtually any flammable elastomeric or polymeric material by techniques which are standard or known to those skilled in the art. See, for example, J. M. Lyons, "The Chemistry and Uses of Fire Retardants", Wiley-Interscience, New York, 1970 and Z. E. Jolles, "Bromine and Its Compounds", Academic Press, New York, 1966. Depending on the substrate and the amount of flame retardancy desired, up to about 50 weight percent of the flame retardant compounds of formula II within the scope of this invention can be incorporated therewith. However, in most applications it is preferably to use less than 25 weight percent of said compounds within the scope of this invention. It should be noted that the optimum level of additive of the flame retardant II within the scope of this invention depends upon the particular substrate being treated as well as the level of flame retardancy desired. For example, in polyurethanes a flame retardant level of from about 10 to about 30 parts per hundred parts polyol is satisfactory. In styrenic polymers, e.g., polystyrene or acrylonitrile/butadiene/styrene terpolymers, epoxy resins and unsaturated polyester resins (non-fiber resins) the amount used is from about 1 to 25% by weight of flame retardant and preferably from 5 to 20% by weight, based on the total composition. Additionally the flame retardancy can be enhanced by the addition of from 1 to 10% by weight of an oxide or halide of the metals of Groups IVA and VA of the Periodic Table, i.e., oxides and halides antimony, tin, bismuth, arsenic, lead, germanium, e.g., antimony trioxide, antimony oxychloride and the like as well as those disclosed in U.S. Pat. Nos. 3,205,196 and 3,894,988 incorporated herein by reference.

The following examples are provided for the purpose of further illustration only and are not intended to be limitations on the disclosed invention. Unless otherwise specified, all temperatures are expressed in degrees centigrade; all weights are expressed in grams; and all volumes are expressed in millimeters.

PREPARATION OF INTERMEDIATES

EXAMPLE 1

Preparation of N-methyloltetrabromophthalimide

Tetrabromophthalimide (30 gm) was suspended in 100 ml of ethanol and 50 gm of 38 percent formaldehyde was added. Then the solution was stirred and heated for three hours at 85° C. Upon cooling, the product was filtered yielding 28 gm of a white solid having a melting point greater than 350° C. The infrared spectrum of the product showed the disappearance of the imide NH and the appearance of an OH absorption at 3450 cm⁻¹. Analysis: Calculated for $C_9H_3Br_4NO_3$; Br, 64.8; hydroxyl number: 89.0; Found: Br, 63.28; hydroxyl number: 90.45.

EXAMPLE 2

Preparation of N-(2-hydroxyethyl) tetrabromophthalimide

To a suspension of 464 gm (1 mole) of tetrabromophthalic anhydride in 1.2 liters of xylene was added 61 gm (1 mole) of ethanolamine. The solution was heated and refluxed with a Dean-Stark water separator until the theoretical amount of water separated. The mixture was cooled, diluted with hexane, and filtered. The resulting 413 gm of an off-white solid was washed with hexane and dried at 100° C. This material is used as is for subsequent reactions without further purification.

THE INVENTION

EXAMPLE 3

Preparation of tris(tetrabromophthalimidoethyl)phosphate (Table I, compound 9)

A suspension of 203 gm of N-(2-hydroxyethyl)tetrabromophthalimide prepared in Example 2, in 200 ml of xylene was treated with 20.6 gm of phosphoryl chloride and 0.5 gm of magnesium oxide catalyst was added. The solution was heated 1 hour at 110° C. and then 5 hours at 134° C. until the evolution of hydrogen chloride ceased. Hexane was added upon cooling and the product was filtered. The tanned solid was washed successfully with hexane and acetone, and dried at 100° C. and one millimeter of mercury for 2 hours. Analysis: Calculated for $C_{30}H_{12}Br_{12}N_3O_{10}P$: Br, 61.2; Found: Br, 63.37.

EXAMPLE 4

Preparation of bis-(2,3-dibromopropyl)-tetrabromophthalimidoethyl phosphate (Table I, compound 10)

A mixture of 181 gm of bis-(2,3-dibromopropyl)-chlorophosphate, 177 gm of N-(2-hydroxyethyl)tetrabromophthalimide, 0.5 gm of magnesium oxide catalyst and 800 ml of xylene was heated slowly to 75° C. Hydrogen chloride evolution became apparent and the mixture was held at this temperature for 1 hour. The temperature was then raised to 120° C. for 2 hours until the evolution of hydrogen chloride ceased. Hexane was added and the product precipitated. Upon filtering, the product was washed at 40° C. with aqueous ammonia, followed by two water washes. An off-white solid having a melting point of 175° to 177° C. resulted. The product was identified by infrared. Analysis: Calculated for $C_{16}H_{14}Br_8NO_6P$: Br, 64.7; Found: Br, 61.9.

EXAMPLE 5

A foam was prepared using the following basic formulation:

| Component | Parts by Weight |
| --- | --- |
| Polyol[a] | 100 |
| Silicone Glycol[b] Surfactant | 2 |
| Trichlorofluoromethane[c] | 35 |
| Polyisocyanate[d] | 135 |

[a]alkanolamine polyol, molecular weight approximately 3500, hydroxyl number approximately 530, Thanol R-350-X, Jefferson Chemical Co., Houston, Texas.
[b]Dow Corning 193, Dow Corning Corp., Midland, MI.
[c]Freon 11B, E.I. Du Pont de Nemours & Co., Wilmington, DE.
[d]Polymeric aromatic isocyanate, 31.5% available NCO, Mondur MRS, Mobay Chemical Co., Pittsburgh, PA.

The polyol, surfactant, and flurocarbon blowing agent were combined in a masterbatch based on 1000 gm of polyol to minimize loss of blowing agent.

The following procedure was used to prepare the foam:

1. The polyisocyanate was weighed into a tared, 10 ounce, paper cup (allowances being made for hold-up) and the cup set aside while the remaining ingredients were weighed out and mixed.
2. The polyol masterbatch was weighed out, in the proper amount to give 100 grams of polyol, in a one quart, untreated, paper cup.
3. The 10 grams of tris(tetrabromophthalimidoethyl)phosphate were then weighed into the same one quart cup.
4. The contents of the one quart cup were mixed at 1000 rpm for 5 seconds.
5. The polyisocyanate was then added and stirring at 1000 rpm continued for 10 seconds.
6. The mix was poured into a 5-pound, untreated, paper tub and allowed to rise.

After the foam was tack-free, and substantially cured, it was set aside for at least seven days prior to subjecting said foam to an Oxygen Index Test, ASTM D-2863-74. The results of said test are reported in Table II, infra.

The same procedure was used to make other foams at different load levels and sometimes also containing a different flame retardant additive. These foams were also subjected to the same Oxygen Index Test as the above foam and the data are also reported in Table II.

TABLE II

| Flame Retardant | Load Level, php[a] | OI |
| --- | --- | --- |
| Control | 0 | 20.5 |
| Tris(tetrabromophth-imidoethyl)phosphate (of Example 3) | 10 | 22.0 |
| | 20 | 23.0 |
| | 30 | 24.5 |
| Bis(2,3-dibromopropyl)-tetrabromophthalimido-ethyl phosphate (of Example 4) | 10 | 22.5 |
| | 20 | 23.5 |
| | 30 | 24.5 |

[a]php means parts per hundred polyol.

EXAMPLE 6

Tris(tetrabromophthalimidoethyl)phosphate (15% of the total mixture by weight; Table I, compound 9) was dry mixed with acrylonitrile/butadiene/styrene (ABS) resin (80% by weight, and 5% by weight antimony oxide). (Cycolac T-2098 brand ABS resin, Borg-Warner Chemicals, Parkersburg, W.Va.) The mixture was passed through a ¾-inch Braebender extruder under the following extrusion conditions: screw speed: 50 rotations per minute (rpm); barrel temperature: back: 370° F., middle: 400° F., front: 400° F.; and die temperature: 370° F. The extrudate out of the extrusion die was cooled, ground and then injection molded using a 30-ton Newberry 1 ounce injection molding machine under the following parameters: screw speed: 280 rpm; injection pressure: initial: 2000 pounds per square inch (psi), secondary; 100 psi; back pressure: 450 psi; stroke pressure: 300 psi; internal barrell temperature: rear zone: 420° F., front zone: 450° F.; cycle time: 60 seconds (sec.); total injection time: 20 sec.; total stroke time: 5 sec. The final ABS polymeric composition was subjected to various tests and the data obtained therefrom are reported in Table III.

Compositions containing bis(2,3-dibromopropyl)tetrabromophthalimidoethyl phosphate (Table I, compound 10) or tetrabromophthalimide, a prior art flame retardant, were also prepared by the above procedures, except that the tetrabromophthalimide had an injection molding stroke pressure of 350 psi, a difference which has no impact on the flame retardant efficacy of the additive. The test data are also reported in Table III.

TABLE III

| | ABS$^a$ Flame Retardant Data | | | |
|---|---|---|---|---|
| | Control | Tris(tetrabromo-phthalimidoethyl)-phosphate | Bis(2,3-dibromo-propyl)tetrabromo-phthalimidoethyl phosphate | Tetrabromo-phthalimide (comparative) |
| Percent Flame Retardant$^b$ | 0 | 15 | 15 | 15 |
| Percent Actionary Oxide$^b$ | 0 | 5 | 5 | 5 |
| UL-94$^c$ | HB | V-O | V-O | V-2 |
| Oxygen Index$^d$, % | 19 | 29 | 27.5 | 27.0 |

$^a$ABS means acrylonitrile/butadiene/styrene terpolymers.
$^b$By weight of total polymeric composition.
$^c$UL-94, Underwriters' Laboratories, Inc., 1973.
$^d$Oxygen Index, ASTM D-2863-74.

With reference to the present invention, one of the critical features of the ABS plastic compositions containing flame retardants within the scope of this invention, as exemplified by tris(tetrabromophthalimidoethyl)phosphate and bis(2,3-dibromopropyl)tetrabromophthalimidoethyl phosphate, is the unusually high flame retardancy thereof. The significance of flame retardancy of plastic compositions is well recognized in the art as heretofore mentioned. However, recent developments in conjunction with the use of flame retardant plastic compositions as judged by the Consumer Product Safety Commission, require a UL-94 value of V-O in order to produce a commercially acceptable article of manufacture. The Consumer Product Safety Commission is continuing to set mandatory standards in the field where the plastic compositions are utilized and since about 1970 has increased the criticality of the UL value of plastic compositions. In reacting to the Consumer Product Safety Commission's mandatory standards in this area, the producers of (plastic composition) articles of manufacture are now requiring that said articles have a V-O value in order to meet new mandatory standards which are anticipated to be activated by federal legislation shortly. Thus, the significance of a plastic composition having a V-O value is well recognized in the art; note Modern Plastics, September 1974, pages 74–77 and which publication is to be considered as incorporated herein by reference.

Based on this disclosure many other modifications and ramifications will naturally suggest themselves to those skilled in the art. These are intended to be comprehended as within the scope of this invention.

The embodiments of the invention in which an exclusive property or privilege is claimed are defined as follows:

1. A flame retardant compound of the formula

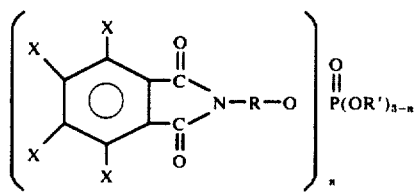

wherein each X is independently selected from chlorine or bromine, R is an alkylene group containing from 1 to 6 carbon atoms, each R' is independently selected from an alkyl or haloalkyl group containing from 2 to 6 carbon atoms, and wherein the haloalkyl group contains from 1 to 3 halogen atoms independently selected from the group comprising chlorine and bromine, and wherein $n$ is 1 to 3.

2. The flame retardant compound of claim 1 wherein R contains from 1 to 3 carbon atoms, wherein R' contains from 2 to 3 carbon atoms, wherein said haloalkyl group contains from 1 to 2 halogen atoms, and when there are two R' groups present in the compound they are the same R' substituent.

3. The flame retardant compound of claim 2 of the formula

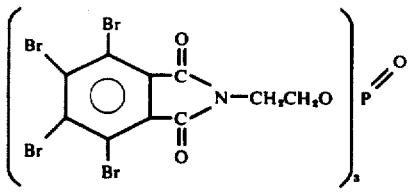

4. The flame retardant compound of claim 2 of the formula

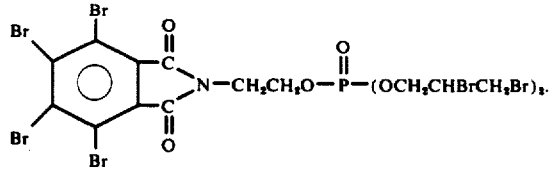

5. A polymeric composition comprising a polymer and a flame retarding amount of the flame retardant compound of claim 1 wherein said polymer is selected from polyurethane, polystyrene and acrylonitrile/butadiene/styrene terpolymers.

6. The polymeric composition of claim 5 wherein R contains from 1 to 3 carbon atoms, wherein R' contains from 2 to 3 carbon atoms, wherein said haloalkyl group contains from 1 to 2 halogen atoms, and when there are two R' groups present in the compound they are the same R' substituent.

7. The polymeric composition of claim 6 wherein said polymer is an acrylonitrile/butadiene/styrene terpolymer.

8. The polymeric composition of claim 6 wherein said polymer is polyurethane.

9. The polymeric composition of claim 6 wherein said polymer is polystyrene.

10. The polymeric composition of claim 8 wherein the polyurethane is a foamed polyurethane.

11. The polymeric composition of claim 9 wherein the polystyrene is a foamed polystyrene.

* * * * *